United States Patent
Berger et al.

(10) Patent No.: US 10,461,124 B2
(45) Date of Patent: Oct. 29, 2019

(54) ULTRASONIC SENSING DEVICE

(71) Applicant: InvenSense, Inc., San Jose, CA (US)

(72) Inventors: Renata Melamud Berger, Palo Alto, CA (US); Julius Ming-Lin Tsai, San Jose, CA (US); Stephen Lloyd, Los Altos, CA (US)

(73) Assignee: InvenSense, Inc., San Jose, CA (US)

( * ) Notice: Subject to any disclaimer, the term of this patent is extended or adjusted under 35 U.S.C. 154(b) by 127 days.

(21) Appl. No.: 15/670,976

(22) Filed: Aug. 7, 2017

(65) Prior Publication Data

US 2019/0043920 A1    Feb. 7, 2019

(51) Int. Cl.

| | |
|---|---|
| *G01N 29/24* | (2006.01) |
| *H01L 41/113* | (2006.01) |
| *G06K 9/00* | (2006.01) |
| *H01L 41/08* | (2006.01) |
| *H01L 27/20* | (2006.01) |
| *G01N 29/28* | (2006.01) |
| *B81C 1/00* | (2006.01) |

(52) U.S. Cl.
CPC .......... *H01L 27/20* (2013.01); *B81C 1/00246* (2013.01); *G01N 29/2437* (2013.01); *G01N 29/28* (2013.01); *G06K 9/0002* (2013.01); *H01L 41/0825* (2013.01); *H01L 41/1132* (2013.01); *H01L 41/1138* (2013.01)

(58) Field of Classification Search
CPC .. G01N 29/2437; G01N 29/28; G06K 9/0002; H01L 27/20; H01L 41/0825; H01L 41/098; B06B 1/0622
See application file for complete search history.

(56) References Cited

U.S. PATENT DOCUMENTS

| | | | | |
|---|---|---|---|---|
| 2007/0272020 | A1* | 11/2007 | Schneider | G01N 29/06 73/628 |
| 2011/0215150 | A1* | 9/2011 | Schneider | G06K 9/0002 235/439 |
| 2014/0145244 | A1* | 5/2014 | Daneman | B81C 3/001 257/254 |
| 2015/0097468 | A1* | 4/2015 | Hajati | H01L 41/0825 310/334 |
| 2015/0298965 | A1* | 10/2015 | Tsai | B81C 1/00182 257/415 |
| 2015/0357375 | A1* | 12/2015 | Tsai | H01L 27/20 257/416 |
| 2016/0117541 | A1* | 4/2016 | Lu | G06K 9/0002 382/124 |
| 2017/0322290 | A1* | 11/2017 | Ng | A61B 5/1172 |
| 2017/0326591 | A1* | 11/2017 | Apte | B06B 1/0292 |

(Continued)

*Primary Examiner* — Helen C Kwok (57) ABSTRACT

An electronic device comprises a CMOS substrate having a first surface and a second surface opposite the first surface. A plurality of ultrasonic transducers is provided having a transmit/receive surface. A contact surface is piezoelectrically associated with the plurality of ultrasonic transducers and is formed on the first surface of the CMOS substrate. The plurality of ultrasonic transducers is disposed on the second surface of the CMOS substrate, with the transmit/receive side attached to the second surface thereof such that the CMOS substrate is between the plurality of ultrasonic transducers and the platen. An image sensing system is also provided, together with a method for ultrasonic sensing in the electronic device.

20 Claims, 8 Drawing Sheets

(56) References Cited

U.S. PATENT DOCUMENTS

2017/0326594 A1* 11/2017 Berger ................. B06B 1/0662
2017/0360399 A1* 12/2017 Rothberg ............. A61B 8/4477
2017/0364726 A1* 12/2017 Buchan ............. G01N 29/2437
2018/0207682 A1*  7/2018 Eovino ................ B06B 1/0666
2019/0005300 A1*  1/2019 Garlepp ................. B06B 1/064

* cited by examiner

ULTRASONIC SENSING DEVICE

BACKGROUND

Piezoelectric materials facilitate conversion between mechanical energy and electrical energy. Moreover, a piezoelectric material can generate an electrical signal when subjected to mechanical stress, and can vibrate when subjected to an electrical voltage. Piezoelectric materials are widely utilized in piezoelectric ultrasonic transducers to generate acoustic waves based on an actuation voltage applied to electrodes of the piezoelectric ultrasonic transducer.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

DESCRIPTION OF EMBODIMENTS

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "transmitting," "receiving," "sensing," "generating," "imaging," or the like, refer to the actions and processes of an electronic device such as an electrical device.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example systems described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As is employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

Overview of Discussion

Discussion begins with a description of an example Piezoelectric Micromachined Ultrasonic Transducer (PMUT), in accordance with various embodiments. Example arrays including PMUT devices are then described. Example operations of the example arrays of PMUT devices are then further described.

A conventional piezoelectric ultrasonic transducer able to generate and detect pressure waves can include a membrane with the piezoelectric material, a supporting layer, and electrodes combined with a cavity beneath the electrodes. Miniaturized versions are referred to as PMUTs. Typical PMUTs use an edge anchored membrane or diaphragm that maximally oscillates at or near the center of the membrane at a resonant frequency (f) proportional to $h/\alpha^2$, where h is the thickness, and $\alpha$ is the radius of the membrane. Higher frequency membrane oscillations can be created by increasing the membrane thickness, decreasing the membrane radius, or both. Increasing the membrane thickness has its limits, as the increased thickness limits the displacement of the membrane. Reducing the PMUT membrane radius also has limits, because a larger percentage of PMUT membrane area is used for edge anchoring.

Embodiments describes herein relate to a PMUT device for ultrasonic wave generation and sensing. In accordance with various embodiments, an array of such PMUT devices is described. The PMUT includes a substrate and an edge support structure connected to the substrate. A membrane is connected to the edge support structure such that a cavity is defined between the membrane and the substrate, where the membrane is configured to allow movement at ultrasonic frequencies. The membrane includes a piezoelectric layer and first and second electrodes coupled to opposing sides of the piezoelectric layer. An interior support structure is disposed within the cavity and connected to the substrate and the membrane.

The described PMUT device and array of PMUT devices can be used for generation of acoustic signals or measurement of acoustically sensed data in various applications, such as, but not limited to, medical applications, security systems, biometric systems (e.g., fingerprint sensors and/or motion/gesture recognition sensors), mobile communication systems, industrial automation systems, consumer electronic devices, robotics, etc. In one embodiment, the PMUT device can facilitate ultrasonic signal generation and sensing (transducer). Moreover, embodiments describe herein provide a sensing component including a silicon wafer having a two-dimensional (or one-dimensional) array of ultrasonic transducers.

Embodiments described herein provide a PMUT that operates at a high frequency for reduced acoustic diffraction through high acoustic velocity materials (e.g., glass, metal), and for shorter pulses so that spurious reflections can be time-gated out. Embodiments described herein also provide a PMUT that has a low quality factor providing a shorter ring-up and ring-down time to allow better rejection of spurious reflections by time-gating. Embodiments described herein also provide a PMUT that has a high fill-factor providing for large transmit and receive signals.

Piezoelectric Micromachined Ultrasonic Transducer (PMUT)

Systems and methods disclosed herein, in one or more aspects provide efficient structures for an acoustic transducer (e.g., a piezoelectric actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

Figure 1A:
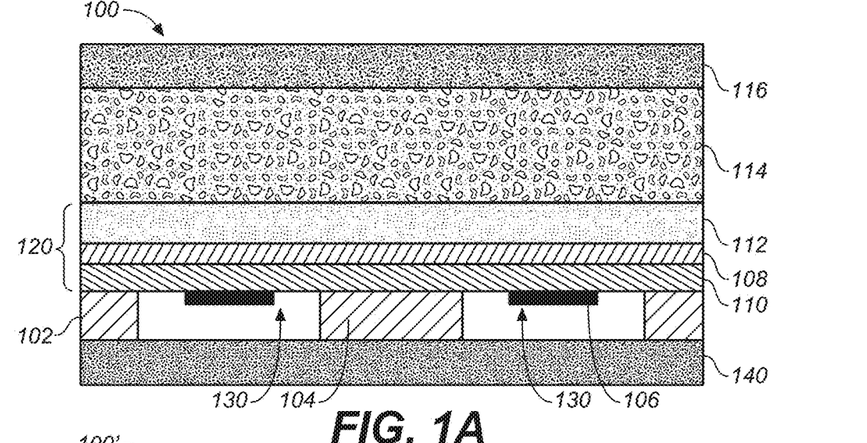
FIG. 1A is a diagram illustrating a piezoelectric micromachined ultrasonic transducer (PMUT) device having a center pinned membrane, according to some embodiments.

FIG. 1A is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections the sides or in vias through edge support 102 or interior support 104, electrically coupling first electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes first electrode 106, piezoelectric layer 110, and second electrode 108, where first electrode 106 and second electrode 108 are coupled to opposing sides of piezoelectric layer 110. As shown, first electrode 106 is coupled to a lower surface of piezoelectric layer 110 and second electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 112 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 1B:
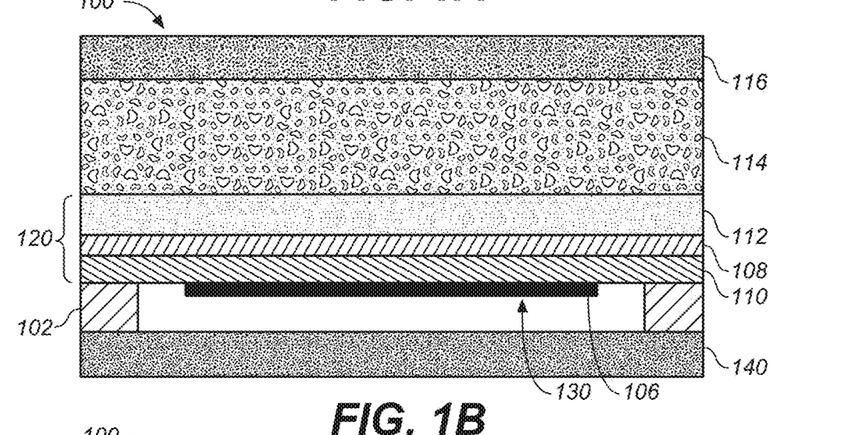
FIG. 1B is a diagram illustrating a PMUT device having an unpinned membrane, according to some embodiments.

FIG. 1B is identical to FIG. 1A in every way, except that the PMUT device 100' of FIG. 1B omits the interior support 104 and thus membrane 120 is not pinned (e.g., is "unpinned"). There may be instances in which an unpinned membrane 120 is desired. However, in other instances, a pinned membrane 120 may be employed.

Figure 2:
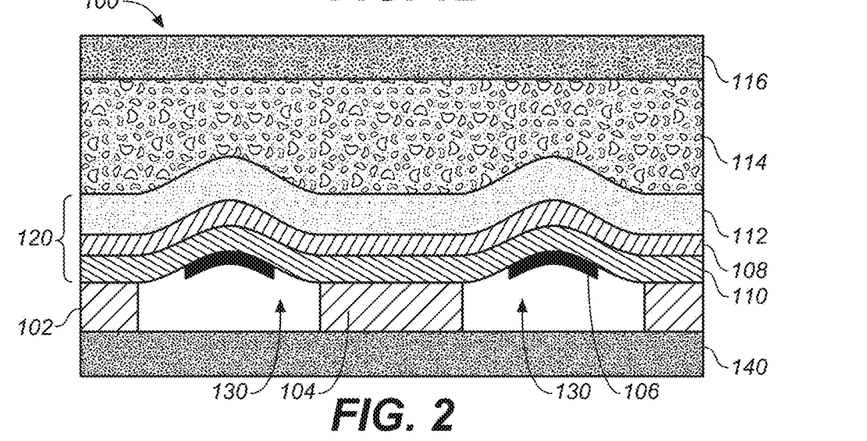
FIG. 2 is a diagram illustrating an example of membrane movement during activation of a PMUT device having a center pinned membrane, according to some embodiments.

FIG. 2 is a diagram illustrating an example of membrane movement during activation of pinned PMUT device 100, according to some embodiments. As illustrated with respect to FIG. 2, in operation, responsive to an object proximate the platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to) distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control, and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, aluminum nitride (AlN), lead zirconate titanate (PZT), scandium doped aluminum nitride (ScAlN), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, the first electrode 106 is a patterned electrode and the second electrode 108 is a continuous electrode. As an example, electrodes 106 and 108 can be comprised of almost any metal layers or other conducting material, such as, but not limited to, aluminum (Al), titanium (Ti), molybdenum (Mo), etc., which are coupled with an on opposing sides of the piezoelectric layer 110. In one embodiment, PMUT device also includes a third electrode (not shown).

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 Mega Rayleigh (MRayl), such as, but not limited to, plastic, resin, rubber, Teflon, epoxy, etc. In another example, the platen layer 116 can comprise various materials having a high acoustic impedance (e.g., an acoustic impendence greater than 10 MRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$ Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, titanium nitride (TiN), silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., aluminum (Al), titanium (Ti), molybdenum (Mo), etc.) patterned to form first electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, the second electrode 108 can be formed as a continuous layer providing a ground plane in contact with mechanical support layer 112, which can be formed from silicon or other suitable mechanical stiffening material. In still other embodiments, the first electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

A potential issue with the above-described design is that the sound waves travel through the epoxy, which has a low acoustic impedance and is not well matched with hard cover materials such as glass or metal. Also, reflection from the backside of the CMOS can also give unwanted reflections. This means that the epoxy thickness and properties have to be controlled very well, and changing thickness is costly in terms of fabrication molds and other features.

The PMUT device 100 as discussed in FIGS. 1A-1B and 2 is designed to transmit the acoustic waves to platen 116, and may be used to image objects in contact with platen 116. As such, PMUT device 100 detects the acoustic waves that are reflected from the object in contact with platen 116. In addition to the acoustic waves transmitted to the platen and the object, acoustic waves are also transmitted into substrate 140, for example, through edge support 102 and interior support 104 which are in contact with substrate 140. Any acoustic waves that enter the substrate may get reflected at any boundary with a change in acoustic impedance. Therefore, many acoustic waves could reflect from the backside of the substrate, and may finally be detected by the PMUT structure. Thus, the acoustic waves from the substrate and the acoustic waves from the object on the platen may both be detected at the same time. This means that any image of the object and the 'image' of the back side of substrate will be superimposed and this negatively influence the image quality of the object on the platen. The CMOS substrate itself is made up of different (metal) layers, but because the acoustic impendences of these layers are nearly identical, only minor acoustic reflection takes place.

In order to overcome the above-mentioned problems, and in accordance with the teachings herein, an electronic device is provided with an inverted design compared with the design depicted in FIGS. 1A-1B and 2. The electronic device with the inverted layout comprises a CMOS substrate having a first surface and a second surface opposite the first surface. A plurality of ultrasonic transducers is provided, having a transmit/receive surface. A platen having a contact surface is piezoelectrically associated with the plurality of ultrasonic transducers and is formed on the first surface of the CMOS substrate. The term "piezoelectrically associated with" refers to a piezoelectric device that uses the piezoelectric effect to measure changes in pressure, acceleration, temperature, strain, or force by converting them to an electrical charge. In the context as used herein, any object in contact with the contact surface of the platen may be imaged because the reflected acoustic waves are converted to an electrical charge by the ultrasonic transducers that are piezoelectrically associated with the platen.

The plurality of ultrasonic transducers is disposed on the second surface of the CMOS substrate, with the transmit/receive surface attached to the second surface thereof such that the CMOS substrate is between the plurality of ultrasonic transducers and the platen.

Figure 3:
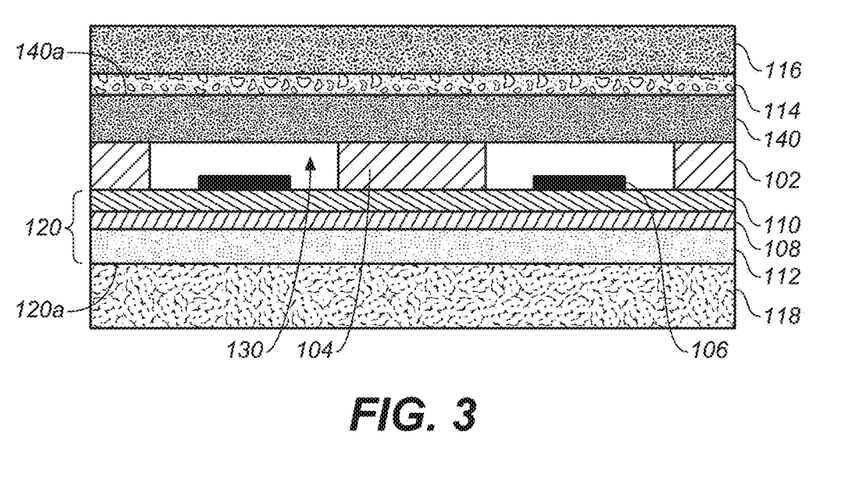
FIG. 3 is a diagram illustrating a configuration of an electronic device having an inverted design, according to some embodiments.

FIG. 3 shows an example of the inverted design, in which the PMUT (or other ultrasonic transducer) transmits ultrasonic signals through the CMOS. All the different layers and component are substantially identical to FIG. 1A. Although the interior support 104 is shown in FIG. 3, it could be omitted, as in FIG. 1B The main differences between FIGS. 1B and 3 lie in the acoustic coupling layers 114 and the acoustic absorption layer 118. The main purpose of acoustic coupling layer 114 in FIG. 3 is to provide contact and adhesion of platen 116 to CMOS substrate 140. If the platen 116 and the CMOS substrate 140 are both hard materials, then small airgaps may occur when both are mounted together, and these air gaps may prevent the transfer of the acoustic waves into the platen 116. If the platen 116 makes perfect contact with the CMOS substrate 140, then no acoustic coupling layer 114 may be needed. This may be the case if the platen 116 is applied in an (initial) liquid- or gel-like form. In some embodiments, the backside 140a of substrate 140 may be used as the contact surface, and no additional platen 116 is required.

Acoustic absorption layer 118 may be applied to the back 120a of membrane 120, which may or may not include mechanical support layer 112. The purpose of acoustic absorption layer 118 is to absorb any acoustic waves that are not transferred into the CMOS substrate 140 and to avoid any acoustic waves transmitted in the "down" direction, so that the acoustic waves are reflected back to the membrane 120 and finally detected. The acoustic absorption layer 118 may also be used as an adhesion or connection layer to fix the PMUT structure to a second substrate, such as, e.g., a PCB (printed circuit board).

Although many of the operating principles of the inverted design and the original non-inverted design are similar, there is an important difference in the generation and transmission of the acoustic waves. In the original design (e.g., FIGS. 1A-1B and 2), the acoustic waves are directly coupled into the acoustic coupling layer 114 due to the vibration of the membrane 120. In the inverted design herein, the acoustic waves are coupled into the CMOS substrate 140 through the vibration of the support structures such as e.g., edge support 102 and interior support 104. As such, the support structures and membrane 120 are designed to optimize the injection of the acoustic waves/energy into the CMOS substrate 140. This means that the shape, size and placement of the support structures 102, 104 are optimized for the acoustic injection. For example, the interior support 104 may be wider than the edge support 102 in order to inject most acoustic energy at the interior support and minimize acoustic injection at the edge supports. The shape of the interior support 104 may, for example, be tapered by this reason. In some embodiments, where a uniform injection of the acoustic energy is required, all support structures 102, 104 may be of similar shape and dimension.

The ultrasonic transducer may be a PMUT device, such as described in connection with FIGS. 1A and 1B, above. Alternatively, the ultrasonic transducer may be a bulk piezo actuator element, such as e.g., lead zirconate titanate (PZT).

Figure 4:
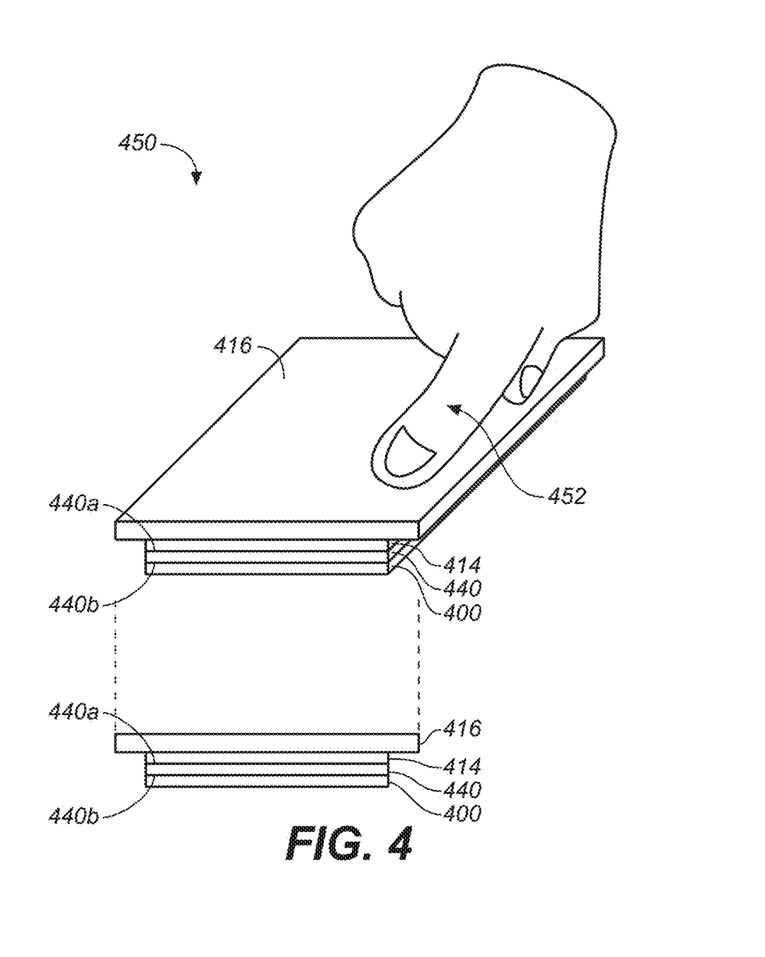
FIG. 4 is a diagram illustrating an ultrasonic transducer used in an ultrasonic fingerprint sensing system, according to some embodiments.

FIG. 4 illustrates an embodiment of an ultrasonic transducer used in an electronic device 450, such as an ultrasonic fingerprint sensing system. The electronic device, or fingerprint sensing system, 450 can include a platen 416 onto which a human finger 452 may make contact. Ultrasonic signals are generated and received by a plurality of ultrasonic transducers 400, such as an array of transducers 400, e.g., a two-dimensional array. The platen 416 is formed on the first, or front, surface 440a of the CMOS substrate 440. An acoustic coupling layer 414, such as a suitable epoxy, secures the platen, 416 to the first surface 440a of the CMOS substrate 440.

The ultrasonic transducer 400 is formed on the second, or back, surface 440b of the CMOS substrate 440 via wafer bonding or other suitable techniques. The ultrasonic signals travel back and forth to the ultrasonic transducer 400 through acoustic coupling layer 414, platen 416, and CMOS substrate 440. Signal analysis is conducted using a processing logic module (e.g., including logic, control, and communication electronics) embedded in the CMOS substrate 440. Furthermore, any logic required to generate and/or detect the acoustic waves using ultrasonic transducer 400 may be embedded in the CMOS substrate. Any connections and/or vias required between the processing logic and ultrasonic transducer may be adapted depending on the specific design and are not shown in the Figures. It will be appreciated that the size of platen 416 and the other elements illustrated in FIG. 4 may be much larger (e.g., the size of a handprint) or much smaller (e.g., just a fingertip) than as shown in the illustration, depending on the particular application. The ultrasonic transducer 400 includes the membrane 120 and exterior support structures 102, and, in some embodiments, the interior support structure 104, described above with reference to FIGS. 1A, 1B, 2, and 3. For clarity, these elements are not shown in FIG. 4.

In this example for fingerprinting applications, the human finger 452 and the processing logic module in the CMOS substrate 440 can determine, based on a difference in interference of the acoustic signal with valleys and/or ridges of the skin on the finger, an image depicting epi-dermis and/or dermis layers of the finger. Further, the processing logic module can compare the image with a set of known fingerprint images to facilitate identification and/or authentication. Moreover, in one example, if a match (or substantial match) is found, the identity of user can be verified. In another example, if a match (or substantial match) is found, a command/operation can be performed based on an authorization rights assigned to the identified user. In yet another example, the identified user can be granted access to a physical location and/or network/computer resources (e.g., documents, files, applications, etc.)

In another example, for finger-based applications, the movement of the finger can be used for cursor tracking/movement applications. In such embodiments, a pointer or cursor on a display screen can be moved in response to finger movement. It is noted that the processing logic module can include or be connected to one or more processors configured to confer at least in part the functionality of the electronic device 350. To that end, the one or more processors can execute code instructions stored in memory, for example, volatile memory and/or nonvolatile memory.

Also in accordance with the teachings herein, an image sensing system includes a CMOS substrate having a first surface and a second surface opposite the first surface and a sensor element comprising a plurality of vibratory devices, such as ultrasonic transducers, a platen, and an acoustic coupling layer. The vibratory devices are formed on the second surface of the CMOS substrate, while the platen is formed over the first surface. The acoustic coupling layer couples the platen to the first surface. The CMOS substrate is between the plurality of ultrasonic transducers and the platen.

Figure 5:
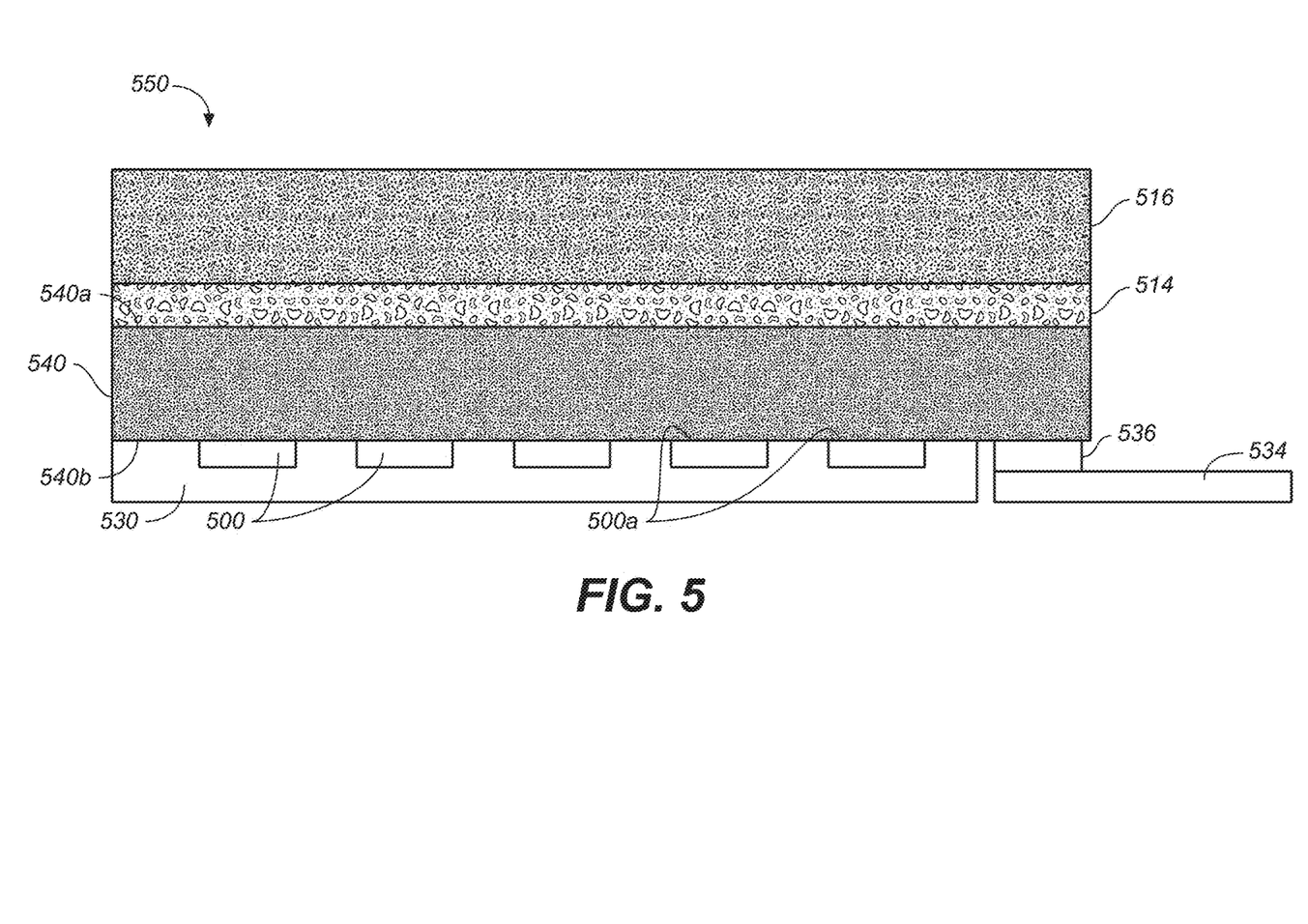
FIG. 5 is a diagram illustrating in cross-section one embodiment of an integrated sensor of the present teachings formed by wafer bonding.

FIG. 5 illustrates in cross section one embodiment of an image sensing system 550 formed by connecting a plurality of ultrasonic devices 500 to the second surface 540*b* of a CMOS logic wafer 540, which includes logic, control, and communication electronics. The ultrasonic devices 500 have a transmit/receive surface 500*a* attached to the second surface 540*b*. Thus, the ultrasonic devices 500 are configured to transmit and receive ultrasonic signals through the second surface 540*b* of the CMOS substrate 540. In an embodiment, a MEMS wafer including the plurality of ultrasonic devices 500 may be wafer-bonded to the second surface 540*b*. In some embodiments, where the ultrasonic devices 500 are PMUT devices, each PMUT device 100 has a membrane 120 formed over a substrate 140 to define a cavity 130, as described above in connection with FIG. 3, for example. The membrane 120, primarily composed of silicon etched along its periphery to form a relatively compliant section, is attached both to a surrounding edge support 102. The membrane 120 is formed from multiple layers, including a piezoelectric layer 110. The sensor may or may not include an interior pinning support 104. In other embodiments the ultrasonic devices 500 are bulk piezo actuator elements, e.g., lead zirconate titanate (PZT).

The CMOS logic wafer 540 has a first, or front, surface 540*a* and a second, or back, surface 540*b* opposite the first surface. The ultrasonic devices 500 are attached to the second surface 540*b*. The platen 516 is attached to the first surface 540*a* via an acoustic coupling material 514, such as a suitable epoxy. The ultrasonic devices 500 may be embedded in an acoustic damping material 530, such as an epoxy. Connection to external circuitry, such as displays, may be made by a flex connector 534 electrically attached to a contact 536. In various embodiments, acoustic waves emanate from the ultrasonic devices 500, through the CMOS logic wafer 540 toward the platen 516.

Figure 6:
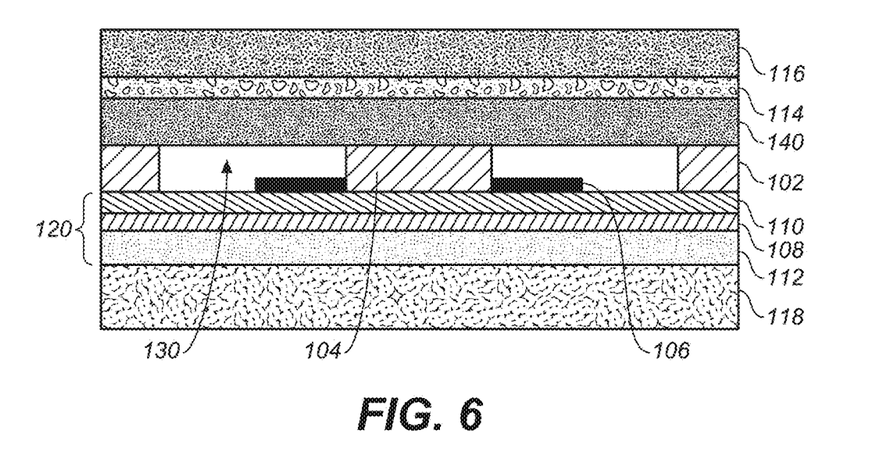
FIG. 6 is a diagram illustrating an alternate embodiment of FIG. 3, in which the electrodes are repositioned in order to increase signal strength, according to some embodiments.

Many variations may be made to enhance the signal strength or other features of the basic device shown in FIG. 3. For example, the electrodes 106 and 108, the piezoelectric layer 110, and mechanical support layer 112 (if present) may also be structured for maximum acoustic injection, for example, by creating maximum leverage of the membrane 120 onto the interior support structure 104. In one embodiment, as shown in FIG. 6, the first electrodes 106 may be positioned closer to the interior support structure 104 for increased signal strength. Alternatively, depending on the desired mode of operation, the first electrodes 106 may be placed closer to edge support structures 102. Piezoelectric layer 110 may be continuous, or may also be structured, as shown in FIG. 7. in order to control the propagation of piezoelectric stress for maximum leverage.

Figure 7:
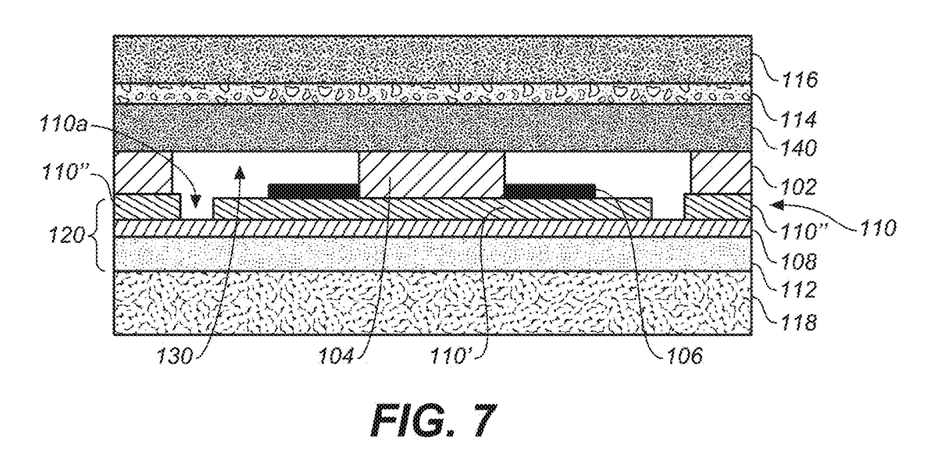
FIG. 7 is a diagram illustrating an alternate embodiment, similar to FIG. 6, in which the ultrasonic membrane is reconfigured to maximize displacement of structures, according to some embodiments.

FIG. 7 is similar to FIG. 6, and FIG. 7 illustrates maximizing displacement of the support structures, here, the interior support structure 104, by altering the membrane 120, such as by creating openings or voids 110*a* in parts of the piezoelectric layer 110, or other parts of membrane 120, to provide a non-uniform but continuous layer. As an alternative to voids, local thickness variations may be used. In this connection, displacement of the piezoelectric layer 110 may be optimized by having the layer thinner in the middle portion and thicker at the edge portion. One or more layers of the membrane may be altered, for example by creating voids or local variations of thickness, with the goal of optimizing the efficiency of the transducer such as by maximizing he displacements of any of the structures used to generate the acoustic energy/waves.

Figure 8:
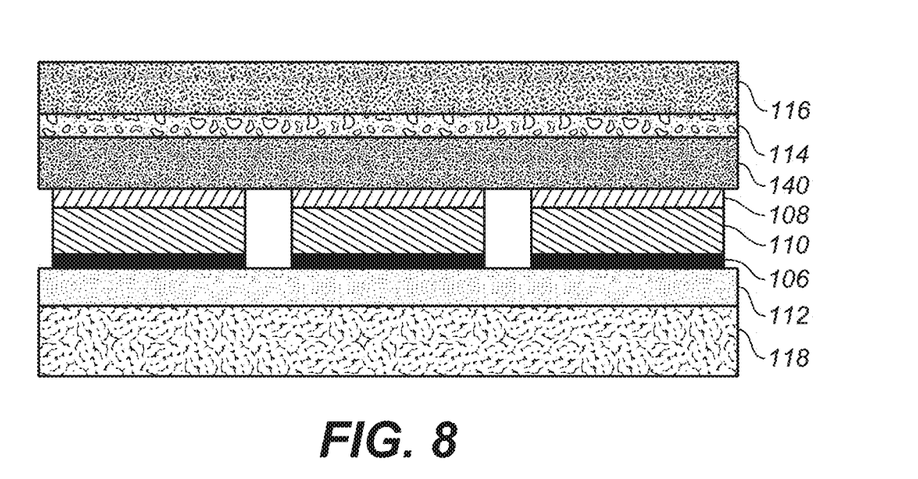
FIG. 8 is a diagram illustrating an alternate embodiment of FIG. 3, in which the PMUT configuration is replaced with a lead zirconate titanate (PZT) structure, according to some embodiments.
Figure 9:
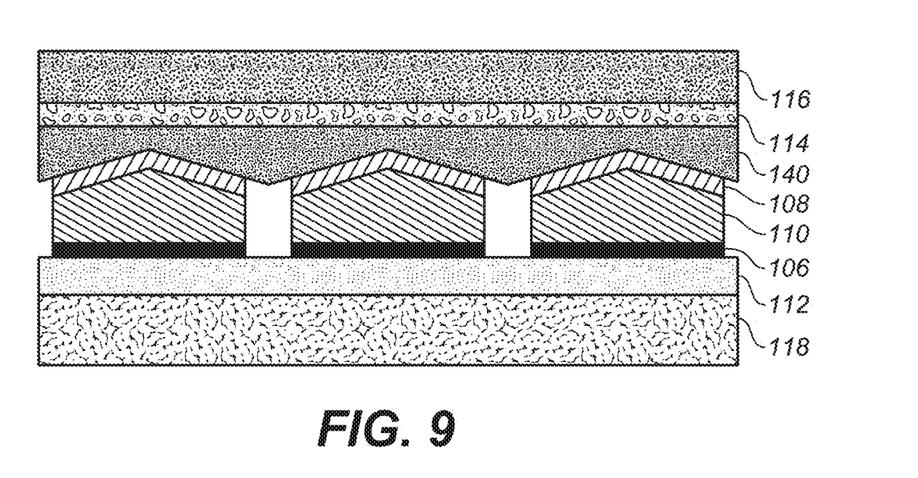
FIG. 9 is a diagram illustrating an embodiment, similar to FIG. 8, in which the shape of the PZT structure is changed, according to some embodiments.

In some embodiments, the membrane-and-cavity design may be replaced by a simpler piezoelectric elements design as shown in FIG. 8. In these embodiments, the piezoelectric layer 110 comprises a layer of bulk piezoelectric material such as, but not limited to, aluminum nitride (AlN), lead zirconate titanate (PZT), scandium doped aluminum nitride (SLAIN), quartz, polyvinylidene fluoride (PVDF), and/or zinc oxide, and is positioned between the first electrode 106 and the second electrode 108, with the second electrode 108 in contact with the substrate 140. An optional mechanical support layer and acoustic absorption layer 118 may be used. The shape of the piezoelectric layer 110 may also be adapted for maximum acoustic injection, for example, as indicated in FIG. 9, which is otherwise similar to FIG. 8.

Figure 10:
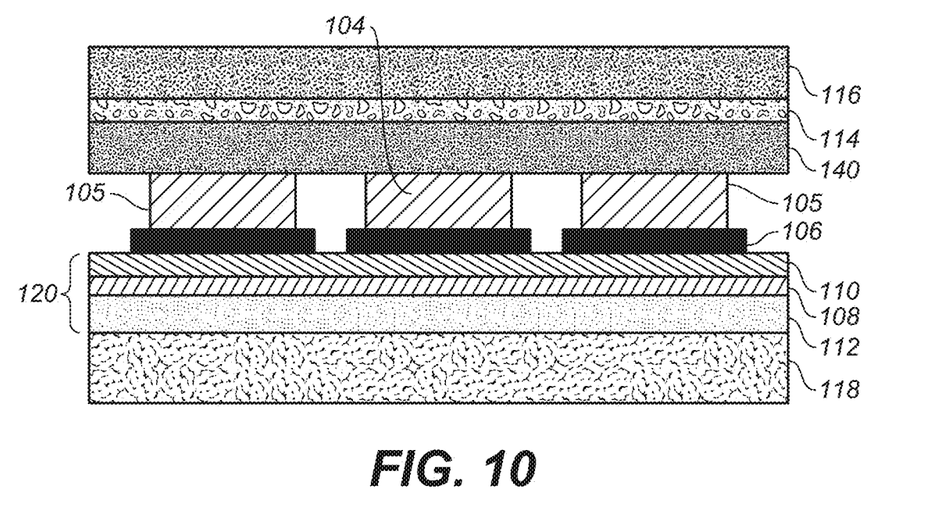
FIG. 10 is a diagram illustrating an alternate embodiment of FIG. 3, employing a hybrid PMUT-PZT structure, according to some embodiments.

In some embodiments, an array of support structures 105 may be deposited between the substrate 140 and the membrane 120, such as shown in FIG. 10. The first electrodes 106 may be structured to address the piezoelectric material associated with the different support structures 104, 105. The structure depicted in FIG. 10 may be considered to a hybrid bulk piezo and -PMUT structure, where the piezoelectric layer 110 is associated with electrodes 106, 108 and the support structures 104, 105 support the CMOS layer 140. The first electrode 106 is beneath the support structure 104, 105 instead of next to it.

The objective is to inject the acoustic waves/energy at the locations of the different support structures 104, 105. The various electrodes 106, 108 and support structures 104, 105 may not only work individually, but in some embodiments an array of structures may work together. For example, some structures may function as transmission structure 104 that generate the acoustic waves and some structures may function as drive structures 105, and the drive structures 105 may be operated to create a maximum of acoustic energy of the acoustic waves at transmission structures 104. One or both of the transmission structures 104 and drive structures 105 may be used to detected the reflected acoustic waves/energy.

Figure 11:
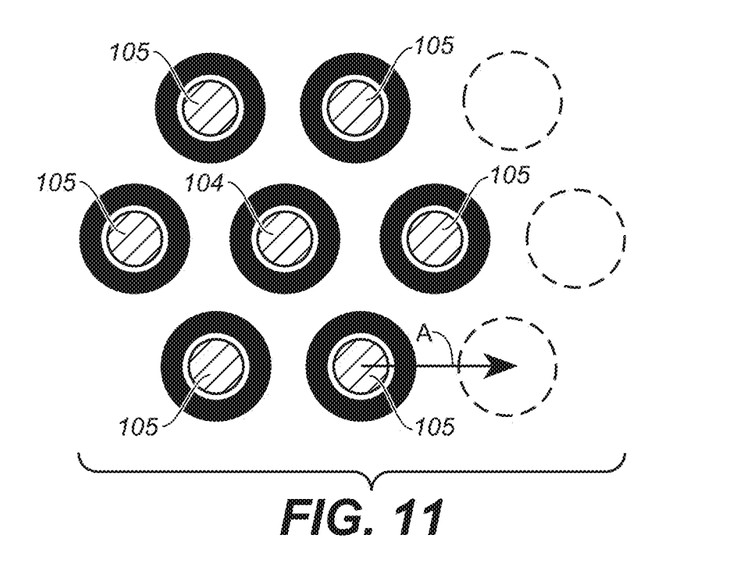
FIG. 11 is a top plan view that illustrates a single transmission structure surrounded by an array of drive structures for increased acoustic injection, according to some embodiments

The drive structures and transmission structures may have an exemplary 2D layout as indicated in FIG. 11, where a single transmission structure is surrounded by an array, here, hexagonal, of drive structures. More complicated patterns using a plurality of rings of drive structures around the transmission structure may be used, and the phase difference of the driving signals of the different structures may be optimized for maximum acoustic injection. By shifting the drive-transmission pattern, other structures may be used as transmission structures, as indicated by arrow A in FIG. 11. The drive structure pins 105 move in a way to maximize displacement of the transmission structure pins 104.

Figure 12:
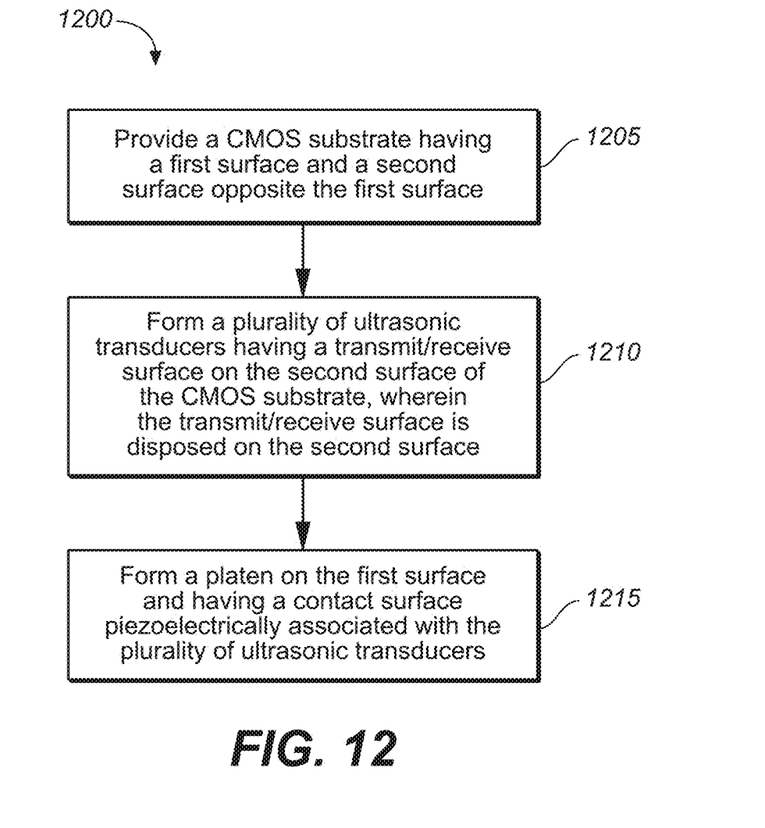
FIG. 12 is a flow chart illustrating one embodiment of a method for ultrasonic sensing in an electronic device.

A method 1200 for ultrasonic sensing using an electronic device 450 is illustrated in FIG. 12. In the method 1200, a CMOS substrate 440 having a first surface 440*a* and a second surface 440*b* opposite the first surface is provided 1205. A plurality of ultrasonic transducers 400 having a transmit/receive surface 400*a* is formed 1210 on the second surface 440*b* of the CMOS substrate 440. The transmit/receive surface 400*a* is disposed on the second surface 440*b*. A platen 416 is formed 1215 on the first surface 440*a* and has a contact surface piezoelectrically associated with the plurality of ultrasonic transducers 400. In this manner, the CMOS substrate 440 is sandwiched between the plurality of ultrasonic transducers 400 and the platen 416.

An acoustic coupling layer 414 may be formed on the first surface 440*a* to which the platen 416 is secured. The acoustic coupling layer 414 may be a suitable epoxy, for example.

The electronic device 450 is configured to sense a fingerprint of a human finger 452. The sensing element may be configured to sense a palm print, a fingertip, or other suitable object.

The plurality of ultrasonic transducers 400 may be at least partly encapsulated in an acoustic damping epoxy (shown as acoustic damping epoxy 530 in FIG. 5).

In the method 1200 for ultrasonic (or image) sensing, acoustic waves may be emitted towards the platen 416 through the CMOS substrate 440. The acoustic waves that reflect off an object 452 on the platen 416 may then be detected and processed by the logic, control, and communication electronics in the CMOS substrate 440.

Example Mobile Electronic Device

Figure 13:
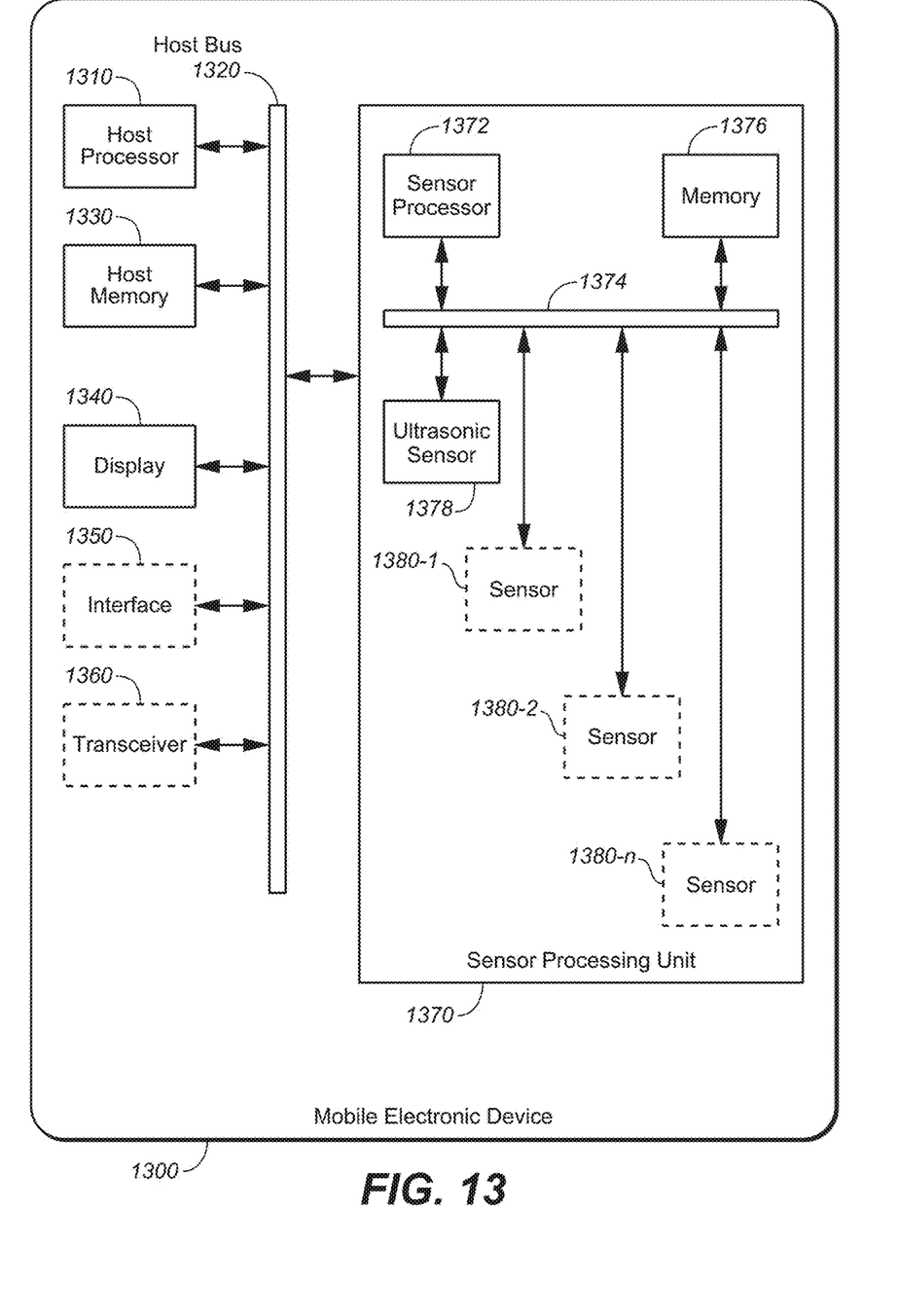
FIG. 13 is a block diagram of an example mobile electronic device upon which embodiments described herein may be implemented.

Turning now to the figures, FIG. 13 is a block diagram of an example mobile electronic device 1300 upon which embodiments described herein may be implemented. As will be appreciated, mobile electronic device 1300 may be implemented as a device or apparatus, such as a handheld mobile electronic device. For example, such a mobile electronic device may be, without limitation, a mobile telephone phone (e.g., smartphone, cellular phone, a cordless phone running on a local network, or any other cordless telephone handset), a wired telephone (e.g., a phone attached by a wire), a personal digital assistant (PDA), a video game player, video game controller, a navigation device, an activity or fitness tracker device (e.g., bracelet, clip, band, or pendant), a smart watch or other wearable device, a mobile internet device (MID), a personal navigation device (PND), a digital still camera, a digital video camera, a portable music player, a portable video player, a portable multi-media player, a remote control, or a combination of one or more of these devices.

As depicted in FIG. 13, mobile electronic device 1300 may include a host processor 1310, a host bus 1320, a host memory 1330, a display device 1340, and a sensor processing unit 1370. Some embodiments of mobile electronic device 1300 may further include one or more of an interface 1350, a transceiver 1360 (all depicted in dashed lines) and/or other components. In various embodiments, electrical power for mobile electronic device 1300 is provided by a mobile power source such as a battery (not shown), when not being actively charged.

Host processor 1310 can be one or more microprocessors, central processing units (CPUs), DSPs, general purpose microprocessors, ASICs, ASIPs, FPGAs or other processors which run software programs or applications, which may be stored in host memory 1330, associated with the functions and capabilities of mobile electronic device 1300.

Host bus 1320 may be any suitable bus or interface to include, without limitation, a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. In the embodiment shown, host processor 1310, host memory 1330, display 1340, interface 1350, transceiver 1360, sensor processing unit (SPU) 1370, and other components of mobile electronic device 1300 may be coupled communicatively through host bus 1320 in order to exchange commands and data. Depending on the architecture, different bus configurations may be employed as desired. For example, additional buses may be used to couple the various components of mobile electronic device 1300, such as by using a dedicated bus between host processor 1310 and memory 1330.

Host memory 1330 can be any suitable type of memory, including but not limited to electronic memory (e.g., read only memory (ROM), random access memory, or other electronic memory), hard disk, optical disk, or some combination thereof. Multiple layers of software can be stored in host memory 1330 for use with/operation upon host processor 1310. For example, an operating system layer can be provided for mobile electronic device 1300 to control and manage system resources in real time, enable functions of application software and other layers, and interface application programs with other software and functions of mobile electronic device 1300. Similarly, a user experience system layer may operate upon or be facilitated by the operating system. The user experience system may comprise one or more software application programs such as menu navigation software, games, device function control, gesture recognition, image processing or adjusting, voice recognition, navigation software, communications software (such as telephony or wireless local area network (WLAN) software), and/or any of a wide variety of other software and functional interfaces for interaction with the user can be provided. In some embodiments, multiple different applications can be provided on a single mobile electronic device 1300, and in some of those embodiments, multiple applications can run simultaneously as part of the user experience system. In some embodiments, the user experience system, operating system, and/or the host processor 1310 may operate in a low-power mode (e.g., a sleep mode) where very few instructions are processed. Such a low-power mode may utilize only a small fraction of the processing power of a full-power mode (e.g., an awake mode) of the host processor 1310.

Display 1340, may be a liquid crystal device, (organic) light emitting diode device, or other display device suitable for creating and visibly depicting graphic images and/or alphanumeric characters recognizable to a user. Display 1340 may be configured to output images viewable by the user and may additionally or alternatively function as a viewfinder for camera.

Interface 1350, when included, can be any of a variety of different devices providing input and/or output to a user, such as audio speakers, touch screen, real or virtual buttons, joystick, slider, knob, printer, scanner, computer network I/O device, other connected peripherals and the like.

Transceiver 1360, when included, may be one or more of a wired or wireless transceiver which facilitates receipt of data at mobile electronic device 1300 from an external transmission source and transmission of data from mobile electronic device 1300 to an external recipient. By way of example, and not of limitation, in various embodiments, transceiver 1360 comprises one or more of: a cellular transceiver, a wireless local area network transceiver (e.g., a transceiver compliant with one or more Institute of Electrical and Electronics Engineers (IEEE) 802.11 specifications for wireless local area network communication), a wireless personal area network transceiver (e.g., a transceiver compliant with one or more IEEE 802.15 specifications for wireless personal area network communication), and a wired a serial transceiver (e.g., a universal serial bus for wired communication).

Mobile electronic device 1300 also includes a general purpose sensor assembly in the form of integrated SPU 1370 which includes sensor processor 1372, memory 1376, an ultrasonic sensor 1378 (e.g., image sensing system 550), and a bus 1374 for facilitating communication between these and other components of SPU 1370. In some embodiments, SPU 1370 may include at least one sensor 1380 (shown as sensor 1380-1, 1380-2, . . . 1380-n) communicatively coupled to bus 1374. In some embodiments, all of the components illustrated in SPU 1370 may be embodied on a single integrated circuit. It should be appreciated that SPU 1370 may be manufactured as a stand-alone unit (e.g., an integrated circuit), that may exist separately from a larger electronic device.

Sensor processor 1372 can be one or more microprocessors, CPUs, DSPs, general purpose microprocessors, ASICs, ASIPs, FPGAs or other processors which run software programs, which may be stored in memory 1376, associated with the functions of SPU 1370.

Bus 1374 may be any suitable bus or interface to include, without limitation, a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. Depending on the architecture, different bus configurations may be employed as desired. In the embodiment shown, sensor processor 1372, memory 1376, sensor 1378, and other components of SPU 1370 may be communicatively coupled through bus 1374 in order to exchange data.

Memory 1376 can be any suitable type of memory, including but not limited to electronic memory (e.g., read only memory (ROM), random access memory, or other electronic memory). Memory 1376 may store algorithms or routines or other instructions for processing data received from ultrasonic sensor 1378 and/or one or more sensor 1380, as well as the received data either in its raw form or after some processing. Such algorithms and routines may be implemented by sensor processor 1372 and/or by logic or processing capabilities included in ultrasonic sensor 1378 and/or sensor 1380.

A sensor 1380 may comprise, without limitation: a temperature sensor, a humidity sensor, an atmospheric pressure sensor, an infrared sensor, a radio frequency sensor, a navigation satellite system sensor (such as a global positioning system receiver), an acoustic sensor (e.g., a microphone), an inertial or motion sensor (e.g., a gyroscope, accelerometer, or magnetometer) for measuring the orientation or motion of the sensor in space, or other type of sensor for measuring other physical or environmental quantities. In one example, sensor 1380-1 may comprise an acoustic sensor, sensor 1380-2 may comprise a second acoustic sensor, and sensor 1380-n may comprise a motion sensor.

In some embodiments, ultrasonic sensor 1378 and/or one or more sensors 1380 may be implemented using a microelectromechanical system (MEMS) that is integrated with sensor processor 1372 and one or more other components of SPU 1370 in a single chip or package. Although depicted as being included within SPU 1370, one, some, or all of ultrasonic sensor 1378 and/or one or more sensors 1380 may be disposed externally to SPU 1370 in various embodiments. It should be appreciated that image sensing system 550 of FIG. 5 is an example of ultrasonic sensor 1378.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. An electronic device comprising:
a CMOS substrate having a first surface and a second surface opposite the first surface;
a plurality of Piezoelectric Micromachined Ultrasonic Transducer (PMUT) devices having a transmit/receive surface, wherein the transmit/receive surface is disposed on the second surface of the CMOS substrate, wherein at least one PMUT device comprises:
an edge support structure connected to the CMOS substrate; and
a membrane connected to the edge support structure such that a cavity is defined between the membrane and the CMOS substrate, the membrane configured to allow movement at ultrasonic frequencies, the membrane comprising:
a piezoelectric layer; and
first and second electrodes coupled to opposing sides of the piezoelectric layer; and
an interior support structure disposed within the cavity and connected to the CMOS substrate and the membrane; and
a contact surface piezoelectrically associated with the plurality of PMUT devices and disposed on the first surface;
wherein the CMOS substrate is between the plurality of PMUT devices and the contact surface.

2. The electronic device of claim 1, wherein at least one of the edge support structure and the interior support structure is configured in at least one of shape, size and placement to optimize acoustic injection into the CMOS substrate.

3. The electronic device of claim 1, wherein the contact surface is a platen.

4. The electronic device of claim 1, further including an epoxy disposed on the second surface of the CMOS substrate and encapsulating the plurality of PMUT devices.

5. The electronic device of claim 4, wherein the epoxy is acoustically damping.

6. The electronic device of claim 1 wherein the contact surface, the CMOS substrate, and the plurality of PMUT devices are configured to operate as a sensor.

7. The electronic device of claim 6, wherein the contact surface is adapted to receive a human finger for sensing a fingerprint.

8. The electronic device of claim 1, wherein the contact surface is acoustically coupled to the first surface of the CMOS substrate.

9. The electronic device of claim 1, wherein the CMOS substrate comprises logic, control, and communication electronics, to which the plurality of PMUT devices is connected.

10. A mobile electronic device comprising:
a host processor;
a host memory; and
an ultrasonic sensor comprising:
a CMOS substrate having a first surface and a second surface opposite the first surface, the CMOS substrate comprising logic, control, and communication electronics;
a plurality of vibratory devices formed on the second surface of the CMOS substrate, each vibratory device comprising a Piezoelectric Micromachined Ultrasonic Transducer (PMUT) device to emit acoustic waves, wherein the PMUT device comprises:
an edge support structure connected to the CMOS substrate; and
a membrane connected to the edge support structure such that a cavity is defined between the membrane and the CMOS substrate, the membrane configured to allow movement at ultrasonic frequencies, the membrane comprising:
a piezoelectric layer; and
first and second electrodes coupled to opposing sides of the piezoelectric layer; and
an interior support structure disposed within the cavity and connected to the CMOS substrate and the membrane; and
a platen formed over the first surface;
wherein the CMOS substrate is between the plurality of vibratory devices and the platen.

11. The mobile electronic device of claim 10, wherein the platen comprises a contact surface adapted to receive a human finger for sensing a fingerprint.

12. The mobile electronic device of claim 10, wherein the ultrasonic sensor is configured to sense a fingerprint of a human finger.

13. The mobile electronic device of claim 10, further including an acoustic coupling layer to couple the platen to the first surface.

14. A method for ultrasonic sensing using an electronic device, the method comprising:
providing a CMOS substrate having a first surface and a second surface opposite the first surface;
forming a plurality Piezoelectric Micromachined Ultrasonic Transducer (PMUT) devices having a transmit/receive side on the second surface of the CMOS substrate, wherein the transmit/receive side is disposed on the second surface, wherein at least one PMUT device comprises:
an edge support structure connected to the CMOS substrate; and
a membrane connected to the edge support structure such that a cavity is defined between the membrane and the CMOS substrate, the membrane configured to allow movement at ultrasonic frequencies, the membrane comprising:
a piezoelectric layer; and first and second electrodes coupled to opposing sides of the piezoelectric layer; and
an interior support structure disposed within the cavity and connected to the CMOS substrate and the membrane; and
forming a platen on the first surface and having a contact surface piezoelectrically associated with the plurality of PMUT devices,
wherein the CMOS substrate is sandwiched between the plurality of PMUT devices and the platen.

15. The method of claim 14 further including forming an acoustic coupling layer on the first surface to which the platen is adhered.

16. The method of claim 14, wherein the PMUT devices and the platen form a sensing element that is configured to sense a fingerprint of a human finger.

17. The method of claim 14 further encapsulating the plurality of PMUT devices in an acoustic damping epoxy.

18. The method of claim 14, further comprising forming logic, control, and communication electronics in the CMOS substrate.

19. The method of claim 14, further comprising causing acoustic waves to be emitted towards the platen through the CMOS substrate.

20. The method of claim 14, further comprising detecting acoustic waves that reflect off an object on the platen.

* * * * *